United States Patent [19]

Bellani et al.

[11] Patent Number: 4,614,744
[45] Date of Patent: Sep. 30, 1986

[54] USE OF FENPYRAMIN AS PLATELET-ANTIAGGREGATING, VASODILATING, ANTITHROMBOTIC AND ANTIANGINOUS MEDICINE

[75] Inventors: Piero Bellani; Gaetano Clavenna, both of Milan; Rinaldo Pellegrini, Treviso, all of Italy

[73] Assignee: RBS Pharma (Roger Bellon Schoum) S.p.A., Milan, Italy

[21] Appl. No.: 631,825

[22] Filed: Jul. 17, 1984

[30] Foreign Application Priority Data

Jul. 25, 1983 [IT] Italy ................ 22221 A/83

[51] Int. Cl.$^4$ ........................... A61K 31/44
[52] U.S. Cl. ..................... 514/277; 514/929
[58] Field of Search .............. 514/277, 929; 424/35

[56] References Cited

U.S. PATENT DOCUMENTS 4,225,602  9/1980  Johnson et al. .................. 514/277

FOREIGN PATENT DOCUMENTS 56-55314  5/1981  Japan .................... 514/277
2051801   1/1981  United Kingdom ........ 514/277

OTHER PUBLICATIONS

Martindale, The Extra Pharmacopoeia, 28th Edition, edited by James E. F. Reynolds, The Pharmaceutical Press, London, 1982, p. 1710.

Primary Examiner—Ronald W. Griffin

[57] ABSTRACT

A new use of N-(4'-pyridyl)-3,3-diphenylpropyl amine, known as fenpyramin, as platelet aggregation-inhibiting medicine and antithrombotic agent as well as vasodilating and antianginous medicine is described.

2 Claims, No Drawings

USE OF FENPYRAMIN AS PLATELET-ANTIAGGREGATING, VASODILATING, ANTITHROMBOTIC AND ANTIANGINOUS MEDICINE

BACKGROUND OF THE INVENTION

The present invention relates to new uses of fenpyramin or N-(4'-pyridyl)-3,3-diphenylpropyl amine hydrochloride of the formula:

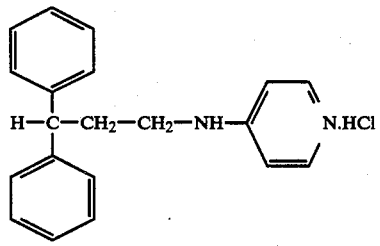

In particular, the present invention relates to the therapeutic use of fenpyramin as a platelet-antiaggregating and antithrombotic as well as vasodilating and antianginous medicine.

DESCRIPTION OF THE PRIOR ART

The spasmolytic, myorelaxing and local anesthetic activity of fenpyramin and its analogous compounds was described and claimed in the Italian patent application No. 20338 A/80 of the same Applicant.

In particular, the above-mentioned fenpyramin is broadly used under various names (Fenprin, Miospasm, etc.) as a spasmolytic agent and its activity is proved by a number of literature references.

SUMMARY OF THE INVENTION

The investigation studies on the characteristics of fenpyramin have lead the applicant to suppose and then to find a remarkable platelet-antiaggregating and vasodilating activity. It was thus proved for instance that fenpyramin modifies in vitro some sub-cellular processes, and more specifically performs some effects on phosphodiesterases, the enzimes metabolizing the cyclic nucleotides. Such an action is of the restraining type, like that of other substances which are generally used as vasodilating and platelet-antiaggregating agents.

Since the clearacteristics phenomenon of thrombosis is the arrangement and settlement of platelets on inner walls of blood vessels, followed by an accumulation of blood cells and fibrin, the therapeutic possibilities can consist of a treatment with anticoagulant, antithrombotic and thrombolytic agents.

From a theoretical point of view, an ideal antithrombotic medicine should be endowed with a preventive action with respect to the thrombus building, rather than with a break down action on the already formed clot. In this perspective, the activity of fenpyramin was evaluated in comparison with the drugs which are regarded at present as most appropriate in this particular therapeutic field.

The activity of fenpyramin was tested in vitro and in vivo as an inhibiting agent of platelet aggregation and inhibiting agent of thrombus building in little vessels by comparison with Naproxen ((+)-6-methoxy-α-methyl-2-naphthalene acetic acid), Dipyridamol (2,2',2'',2'''-(4,8-dipiperidine-pyrimido[5,4-d]pyrimidine-2,6-dinitrile)tetraethanol), Pyridinol carbamate (2,6-pyridine-dimethylene diester of methylcarbamic acid), and Acetylsalicylic acid.

According to these tests it was further shown that fenpyramin has also a remarkable coronarodilating and general vasodilating activity, as well as a negative inotropic activity.

The advantages which can be potentially attained with the combination of such different activities are evident. As a matter of fact, in the case of a thrombotic cardiac infarct, the coronarodilation annihilates the induced spasm, lowers the pain and increases the reduced blood flow, while the negative inotropic action reduces the contractivity thus facilitating the muscular relaxation.

On the other hand the antiaggregating and antithrombotic action can better develop under such circumstances, thus facilitating the reduction or removal of thrombus and consequently the functional recovery and return to the physiologic state.

The present invention will now be illustrated by some examples which are not in any way to be regarded as limitative.

ANTIAGGREGATING ACTIVITY

Example 1

In vitro inhibition of platelet aggregation.

Four human blood samples which were taken through a venous route from as many healthy persons of both sexes were centrifuged, and the supernatant portion consisting of platelets-rich plasma was treated with compounds which notoriously cause the platelet aggregation, such as adenosin-diphosphate (ADP), arachidonic acid and collagen.

To the various samples so treated and suitably subdivided in test tubes there were added in step concentrations fenpyramin and the comparative compounds (Naproxen, Dipyridamol, Pyridinol carbamate and Acetylsalicylic acid) up to reach the lowest dose capable of inhibiting the platelet aggregation.

The reading of the platelet aggregation values was effected according to the Born's method described in Nature, 194, 927, 1962. The obtained range of values is shown in table 1, which takes also into account the biological changes due to the different individual sensibilities or responses.

TABLE 1

| | Effect of fenpyramin HCl and comparative drugs on the platelet aggregation induced in man. | | |
|---|---|---|---|
| | Aggregating agent | | |
| Active substance | ADP | Collagen | Arachidonic acid |
| Fenpyramin | $1 \times 10^{-5}$M to $5 \times 10^{-8}$M | $2.5 \times 10^{-4}$M to $5 \times 10^{-5}$M | $7.5 \times 10^{-4}$M to $5 \times 10^{-5}$M |
| Naproxen | $5.0 \times 10^{-4}$ to $5.0 \times 10^{-6}$M | | |
| Dipyridamol | $5.0 \times 10^{-4}$ to $2.5 \times 10^{-4}$M | | |
| Pyridinol carbamate | $5.0 \times 10^{-4}$ to $2.5 \times 10^{-4}$M | | |

TABLE 1-continued

Effect of fenpyramin HCl and comparative drugs on the platelet aggregation induced in man.

| Active substance | Aggregating agent | | |
|---|---|---|---|
| | ADP | Collagen | Arachidonic acid |
| Acetylsalicylic acid | $1.0 \times 10^{-4}$M (') | | |

(') an activity at concentrations higher than $1 \times 10$ in vitro is not generally regarded as significant.

As it can be seen from the above data, fenpyramin is a drug endowed with a remarkable antiaggregating activity, quite superior to that of the drugs presently used in therapy.

ANTITHROMBOTIC ACTIVITY

Example 2

In vivo inhibition of thrombus building.

The test was carried out on Guinea-pigs after oral administration of fenpyramin and comparative drugs at different doses using the slightly modified method described by Duling et al (Microvascular Research, 1, 158, 1968) and by Begent et al (British Journal of Pharmacology, 43, 580, 1971).

To the anesthesized animal which were maintained at the temperature of 37° C. throughout the whole test, the interior portion of the check was turned inside out to expose the vascular tissue which was kept in a Tyrode solution and observed with a microscope at 250-320 magnifications. Some micropipets containing adenosine diphosphate, a known aggregating agent, were placed closed to venules of 27-40 μm in diameter. When a negative potential was applied to the micropipets, the ADP was expelled at constant velocities and doses causing in about 5-10 seconds the building of platelet thrombi which developed to emboli. The growing velocity of thrombi was determined for 1-2 hours at five minutes intervals after administration of the tested drugs. The extent of inhibition was calculated as a percentage with respect to a control group of Guinea-pigs not treated with any drug.

The obtained results are shown in Table 2.

TABLE 2

Maximum inhibition percentage an appearance times of the first thrombi.

| Dose (mg/kg p.o.) | | Results |
|---|---|---|
| Fenpyramin | 1 mg | 31%; 80 minutes from administration |
| | 3 mg | 38%; 70 minutes from administration |
| | 12 mg | 48%; 70-80 min. from administration |
| Dipyridamol | 2.5 mg | 36%; 45 minutes from administration |
| Papaverin | 3.75 mg | 45%; 70 minutes from administration |
| Acetylsalicylic acid | 15 mg | 40%; 70 minutes from administration |

The reported results clearly show a remarkable antithrombotic activity of fenpyramin, which is in many cases higher than that of the usual inhibiting agents, in particular at lower doses.

CORONARODILATING ACTIVITY

The coronarodilating activity of fenpyramin-HCl was studied evaluating the changes induced in the coronary flow of an "in vitro" specimen. Parallely, the possible effects on strength and frequency of cardiac contraction were controlled. The effects were compared with that which are induced under the same experimental conditions by suitable doses of a drug known for its activity on heart: i.e. papaverin.

The study was carried out on an isolated Guinea-pig heart according to the slightly modified Langendorff's method (O. Langendorff, Arch. Ges. Physiol., 61, 291 (1895)), which allows to evaluate the compounds having a coronarodilating activity.

There were used male spotted Guinea-pigs weighing about 600 g. The animals were previously eparinized by injecting intraperitoneally a dose of the substance corresponding to 500 UI/kg, and subsequently killed by head injury.

The heart was isolated and fixed, according to the chosen procedure, to an aortic cannula of polyethylene connected with the perfusion system, which was filled with a Tyrode solution thermostated at 37° C. and oxygenated with a mixture of $O_2$—$CO_2$ (95-5%). The aortic pressure was kept constant by the weight of the liquid column of 60 cm.

The coronary flow was measured by collecting the perfusional liquid through a funnel system in a calibrated test tube at intervals not lower than a minute.

The strength and frequency of the cardiac contraction were recorded by hooking the apex of the ventricle and connecting it with an isometric strength transducer connected to a microdynamometer (Basile Recording Microdynamometer 7050) provided with a frequency integrating meter. The apparatus was previously adjusted for the transformation of the recorded cm in g of strength.

The activity of fenpyramin-HCl was evaluated after massive bolus administration at doses of: 1-3-10-30 and 100 μg in aortic cannula.

To this purpose the substance was dissolved in Tyrode and administered at a fixed volume of 1 ml. Papaverin was administered at the same doses and according to the same procedures.

The statistic processing of the data was carried out between the previous and consequent average values by the Student "t"-test for coupled data with one tail.

The percent changes with respect to the basal values were also calculated and the effect duration was measured for at least 5' from the treatment.

The activity of fenpyramin-HCl was further tested by continuous infusion at the concentrations of 1 and 100 μg/ml respectively.

RESULTS

Fenpyramin-HCl shows at the used doses a good coronarodilating activity, as it is proved by the coronary flow values shown in Table 3. All the flow increments are statistically significant.

The effect is dose-dependent and appears, as general rule, slightly higher than that found with equal doses of papaverin.

The duration of the coronarodilating effect is almost the same for the two drugs. It exceeds 5 minutes only at the highest employed doses and the action disappears at any rate within 15 minutes from the treatment.

Fenpyramin-HCl further shows a remarkable negative inotropic effect which is statistically significant already at the second dose level employed (Table 4). This behaviour of fenpyramin-HCl clearly strays from the action patterns of papaverin. This substance shows in fact, within the range of all the tested doses, a slight positive inotropic effect which, even not being statistically significant, keeps almost constant for more than 5 minutes.

The action of the two drugs on the cardiac contraction frequency is less significant (Table 5).

The continuous perfusion with fenpyramin-HCl at a concentration of μg/ml causes a remarkable increment of coronary flow which comes back at any rate to basal values within an hour (Table 6). The maximum effect is attained at 3 minutes from the beginning of the perfusion. The substance further produces negative inotropic and chronotropic effects which reach a maximum decrease at 2.5 minutes within the first 5 minutes of treatment.

The prepared specimen recovers then partially its own contractile properties, while subsequently a progressive decrease both of strength and contraction frequency is found.

After washing, the contraction strength goes back to almost basal levels, while the frequency unchanged with respect to the values recorded in the latest treatment steps.

The infusion with fenpyramin-HCl at a concentration of 100 μg/ml brings about within few minutes from the beginning of the treatment the suspension of activity of the prepared specimen.

TABLE 3

Effect on coronary flow

| Product | Dose in μg each bolus | No. of data | Basal flow ml/min M ± E.S. | Maximum recorded effect ml/min M ± E.S. | Change % | Duration of effect min |
|---|---|---|---|---|---|---|
| FENPYRAMIN | 1 | 4 | 4.51± 0.56 | 5.35°± 0.62 | +18.62 | ~2' |
| | 3 | 6 | 4.63± 0.75 | 5.63°± 0.89 | +21.60 | ~3' |
| | 10 | 4 | 4.76± 0.70 | 6.65°± 1.35 | +39.71 | ~3' |
| | 30 | 4 | 4.74± 0.76 | 7.38°± 1.26 | +55.70 | ~2' |
| | 100 | 4 | 4.57± 1.52 | 8.73∞± 1.89 | +91.02 | >5' |
| PAPAVERIN | 1 | 3 | 4.02± 1.16 | 4.10± 1.20 | +2.00 | ~2' |
| | 3 | 3 | 3.87± 1.15 | 4.93°± 1.43 | +27.39 | ~3' |
| | 10 | 3 | 4.76± 1.10 | 6.17°± 1.39 | +29.62 | ~5' |
| | 30 | 3 | 5.81± 1.57 | 8.70∞± 1.50 | +49.74 | >5' |
| | 100 | 3 | 5.90± 1.53 | 10.90∞± 1.79 | +84.75 | >5' |

"t" of Student for coupled data (one tail)
°P < 0.05
∞P < 0.01

TABLE 4

Effect on the cardiac contraction strength

| Product | Dose in μg each bolus | No. of data | Basal contraction g M ± E.S. | Maximum recorded effect g M ± E.S. | Change % | Duration of effect min |
|---|---|---|---|---|---|---|
| FENPYRAMIN | 1 | 4 | 1.74± 0.18 | 1.63± 0.27 | −6.32 | ~2'ϕ |
| | 3 | 6 | 1.69± 0.17 | 1.55°± 0.22 | −8.28 | ~3'ϕϕ |
| | 10 | 4 | 1.27± 0.22 | 1.07°± 0.24 | −15.75 | ~4'ϕ |
| | 30 | 4 | 1.23± 0.22 | 0.79∞± 0.16 | −35.77 | ~4'ϕ |
| | 100 | 4 | 1.29± 0.21 | 0.25∞± 0.07 | −80.62 | >5 |
| PAPAVERIN | 1 | 3 | 1.46± 0.18 | 1.52± 0.20 | +4.11 | >5 |
| | 3 | 3 | 1.46± 0.24 | 1.56± 0.35 | +6.85 | >5 |
| | 10 | 3 | 1.48± 0.20 | 1.60± 0.21 | +8.11 | >5 |
| | 30 | 3 | 1.44± 0.24 | 1.55± 0.27 | +7.64 | >5 |
| | 100 | 3 | 1.41± | 1.56± | +10.64 | >5 |

TABLE 4-continued

| | | | Effect on the cardiac contraction strength | | | |
|---|---|---|---|---|---|---|
| Product | Dose in μg each bolus | No. of data | Basal contraction g M ± E.S. | Maximum recorded effect g M ± E.S. | Change % | Duration of effect min |
| | | | 0.25 | 0.21 | | |

"t" of Student for coupled data (one tail)
*P < 0.05
∞P < 0.01
ϕincrease at first minute in one case
ϕϕincrease in several cases

TABLE 5

| | | | Effect on the cardiac contraction frequency | | | |
|---|---|---|---|---|---|---|
| Product | Dose in μg each bolus | No. of data | Basal frequency strokes/min | Maximum recorded effect strokes/min M ± E.S. | Change % | Duration of effect min |
| FENPYRAMIN | 1 | 4 | 155.00 ± 11.90 | 132.50 ± 7.50 | −14.84 | ~4' |
| | 3 | 6 | 142.50 ± 4.79 | 136.67 ± 3.35 | −4.09 | ~3' |
| | 10 | 4 | 167.50 ± 14.35 | 150.00 ± 14.14 | −10.45 | ~5'ϕϕ |
| | 30 | 4 | 157.50 ± 4.79 | 142.50 ± 12.50 | −9.52 | ~5'ϕϕ |
| | 100 | 4 | 120.00 ± 10.00 | 85.00 ± 23.27 | −29.17 | ~5'ϕϕ |
| PAPAVERIN | 1 | 3 | 150.00 ± 5.77 | 146.67 ± 13.33 | −2.22 | ~2' |
| | 3 | 3 | 160.00 ± 5.77 | 163.33 ± 17.64 | +2.08 | ~3' |
| | 10 | 3 | 143.33 ± 8.82 | 134.00 ± 20.23 | −6.51 | ~5' |
| | 30 | 3 | 150.33 ± 11.26 | 145.33 ± 17.94 | −3.33 | ~5' |
| | 100 | 3 | 150.33 ± 11.25 | 155.00 ± 17.56 | +3.11 | ~5' |

"t" of Student for coupled data (one tail)
ϕϕincrease in several cases

TABLE 6

| | Effect of a fenpyramin infusion (1 μg/ml) on the cardiac function; average of 2 measurements. | | | | | |
|---|---|---|---|---|---|---|
| | Coronary flow | | Contraction strength | | Contraction frequency | |
| Perfusion time | ml/min | Difference % on basal flow | g | Difference % on basal strength | stroke/min | Difference % on basal frequency |
| basal | 5.23 | — | 2.10 | — | 180 | — |
| 1' | 9.00 | +72.08 | 2.07 | −1.43 | 170 | −5.56 |
| 2' | 9.40 | +79.73 | 1.82 | −13.33 | 160 | −11.11 |
| 2.5' | | | 1.76 | −16.19 | 160 | −11.11 |
| 3' | 9.80 | +87.38 | 2.07 | −1.43 | 180 | 0 |
| 4' | 8.50 | +62.52 | 1.99 | −5.24 | 170 | −5.56 |
| 5' | 8.10 | +54.88 | 1.93 | −8.10 | 180 | 0 |
| 15' | 7.00 | +33.84 | 1.60 | −23.81 | 150 | −16.67 |
| 30' | 6.10 | +16.63 | 1.37 | −34.76 | 130 | −27.78 |
| 45' | 5.70 | +8.99 | 1.23 | −41.43 | 120 | −33.33 |
| 60' | 5.30 | +1.34 | 1.26 | −40.00 | 100 | −44.44 |

VASODILATING ACTIVITY

The study was carried out on 10 patients with obliterating arteriopathy of lower extremities at I and II stages according to Fontaine (8 men and 2 women) aged between 49 and 71 years (average 57 years). The patients did not take any drug for ten days prior to the beginning of therapy and followed a normosodic diet.

By pletismography and extensometry the following parameters were evaluated: flow at rest (RF), post-ischaemic hyperaemia (PF), PF onset time (tPF) and its relevant halving time (t ½), total recovery time (tT). There were further measured the basal (RVB) and minimum (RVM) vascular resistencies, the systolic (PAS) and diastolic (PAD) arterial pressure, the calf-measured arterial pressure (PASP), the cardiac frequency (FC) and the Windsor index (I.W.).

The statistic analysis of the data was effected through the Student's "t" for coupled data.

The parameters were evaluated before (B) and after (F) the administration of 110 mg/os/day of fenpyramin (4 tablets of Fenprin, a proprietary medicine) for 15 days.

The obtained results show that fenpyramin is endowed, at the used doses, with a vasodilating activity, as it is shown by the decrease of vascular resistencies and by the increase of bloodflow in the same region.

TABLE 7

Pletismographic examination by extensometer

| No. of patients | Flow at rest (RF) ml min·100 g | | Post-ischaem. hyperaemia (PF) | | Ratio PF/RF | | tPF (sec) | | t½ (sec) | | tT(sec) | | PAS (mmHg) | | PAD (mmHg) | |
|---|---|---|---|---|---|---|---|---|---|---|---|---|---|---|---|---|
| | B | F | B | F | B | F | B | F | B | F | B | F | B | F | B | F |
| 1 | 1,29 | 2,17 | 8,31 | 9,71 | 6,44 | 4,47 | 4,9 | 5,2 | 18,9 | 19,4 | 87,8 | 91,4 | 160 | 160 | 90 | 90 |
| 2 | 1,72 | 2,54 | 9,93 | 12,4 | 5,77 | 4,88 | 7,2 | 6,4 | 25,2 | 23,5 | 93,5 | 98,5 | 160 | 140 | 95 | 90 |
| 3 | 1,45 | 1,89 | 14,2 | 15,6 | 9,79 | 8,25 | 14,4 | 10,5 | 37,4 | 29,2 | 120,1 | 110,9 | 145 | 140 | 85 | 80 |
| 4 | 1,82 | 2,43 | 12,7 | 18,2 | 6,98 | 7,49 | 13,9 | 11,4 | 29,7 | 25,6 | 105,7 | 98,1 | 130 | 130 | 70 | 65 |
| 5 | 1,33 | 1,42 | 9,12 | 11,9 | 6,86 | 8,38 | 10,4 | 8,9 | 21,4 | 20,9 | 98,4 | 102,4 | 140 | 140 | 80 | 80 |
| 6 | 1,52 | 2,08 | 11,05 | 17,2 | 7,27 | 8,27 | 10,9 | 9,2 | 19,3 | 21,3 | 135,6 | 128,6 | 160 | 140 | 100 | 90 |
| 7 | 1,24 | 1,84 | 13,43 | 11,6 | 10,83 | 6,3 | 8,7 | 8,5 | 24,5 | 26,5 | 133,2 | 120,3 | 160 | 150 | 90 | 90 |
| 8 | 1,40 | 2,21 | 12,9 | 11,5 | 9,21 | 5,2 | 12,2 | 11,3 | 17,2 | 15,3 | 144,9 | 150 | 140 | 140 | 85 | 85 |
| 9 | 1,67 | 2,35 | 7,51 | 8,7 | 4,5 | 3,7 | 6,4 | 6,8 | 12,9 | 14,9 | 161,1 | 147,8 | 200 | 145 | 110 | 85 |
| 10 | 1,37 | 2,15 | 10,6 | 9,2 | 7,74 | 4,28 | 9,7 | 5,4 | 27,2 | 21,4 | 142,3 | 122,2 | 150 | 145 | 100 | 95 |
| x̄ | 1,48 | 2,11 | 10,98 | 12,6 | 7,54 | 6,12 | 9,87 | 8,36 | 23,37 | 21,8 | 122,26 | 117,02 | 153,5 | 143 | 90,5 | 85 |
| ± ES. | 0,06 | 0,1 | 0,72 | 1,05 | 0,61 | 0,58 | 0,99 | 0,73 | 2,22 | 1,46 | 7,88 | 6,51 | 6,06 | 2,49 | 3,61 | 2,69 |
| t | 8,5 | | 1,87 | | 2,13 | | 2,92 | | 1,41 | | 1,82 | | 1,96 | | 2,28 | |
| p | <0,001 | | n.s. | | n.s. | | <0,02 | | n.s. | | n.s. | | n.s. | | <0,05 | |

| No. of patients | PAM (mmHg) | | PASP (mmHg) | | I.W. (PASP/PAS) | | RVB (PAM/RF) | | RVM (PAM/PF) | |
|---|---|---|---|---|---|---|---|---|---|---|
| | B | F | B | F | B | F | B | F | B | F |
| 1 | 113,3 | 113,3 | 92 | 94 | 0,58 | 0,59 | 87,8 | 52,2 | 13,6 | 11,7 |
| 2 | 113,3 | 106,7 | 95 | 97 | 0,63 | 0,69 | 65,9 | 42 | 11,4 | 8,6 |
| 3 | 105 | 100 | 88 | 89 | 0,61 | 0,64 | 72,4 | 52,9 | 7,4 | 6,4 |
| 4 | 90 | 86,7 | 76 | 80 | 0,58 | 0,62 | 49,5 | 35,8 | 7,1 | 4,8 |
| 5 | 100 | 100 | 92 | 90 | 0,66 | 0,64 | 75,2 | 70,4 | 11 | 8,4 |
| 6 | 120 | 106,7 | 94 | 95 | 0,59 | 0,68 | 78,9 | 51,3 | 10,9 | 6,2 |
| 7 | 113,3 | 110 | 89 | 95 | 0,56 | 0,63 | 91,4 | 59,8 | 8,4 | 9,5 |
| 8 | 103,3 | 103,3 | 90 | 95 | 0,64 | 0,68 | 73,8 | 46,7 | 8 | 9 |
| 9 | 140 | 105 | 97 | 105 | 0,49 | 0,72 | 83,8 | 44,7 | 18,6 | 12,1 |
| 10 | 116,7 | 111,7 | 93 | 100 | 0,62 | 0,69 | 85,2 | 52 | 11 | 12,1 |
| x̄ | 111,5 | 104,3 | 90,6 | 94 | 0,6 | 0,66 | 76,4 | 50,8 | 10,7 | 8,9 |
| ± ES. | 4,25 | 2,4 | 1,84 | 2,12 | 0,02 | 0,01 | 3,9 | 3,04 | 1,1 | 0,8 |
| t | 2,14 | | 3,43 | | 2,92 | | 7,70 | | 2,32 | |
| p | n.s. | | <0,01 | | <0,02 | | <0,001 | | <0,05 | | x̄ = average values
± ES. = experimental error
t = Student
p = probability
n.s. = not significant Although the present invention was described with particular reference to fenpyramin, it is clear that changes and/or variations can be introduced therein without departing therefore from the spirit and scope of the invention. In particular it will be possible to use for the same purpose and with similar results the fenpyramin derivatives which were described in Italian patent application Nos. 23122 A/79 and 20338 A/80 of the same Applicants, as well as possible further compounds closely similar to fenpyramin from the structural point of view.

Fenpyramin and its analogous compounds as well as the pharmacological acceptable salts thereof can be utilized in human therapy as antiaggregating, antithrombotic and vasodilating agents in pharmaceutical forms for oral use, such as solutions, suspensions, capsules, sugar-coated pills, tablets, and pharmaceutical forms for parenteral administration, such as suppositories and injectable solutions.

In particular, the coronary vasodilating action together with the negative inotropic action make useful the use thereof as antianginous drugs.

What we claim is:

1. Therapeutic use as a platelet-antiaggregating, vasodilating and antianginous medicine of N-(4'-pyridyl)-3,3-diphenyl propylamine hydrochloride (fenpyramin) having formula:

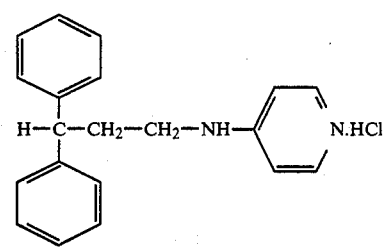

2. A method of promoting blood circulation in a warm-blooded animal, which comprises administering to said animal a therapeutically effective amount of fenpyramin.

* * * * *